(12) United States Patent
Fukuma et al.

(10) Patent No.: US 7,604,351 B2
(45) Date of Patent: Oct. 20, 2009

(54) OPTICAL IMAGE MEASUREMENT DEVICE AND OPTICAL IMAGE MEASUREMENT METHOD

(75) Inventors: Yasufumi Fukuma, Fort Lee, NJ (US); Hisashi Tsukada, Tokyo (JP); Tsutomu Kikawa, Tokyo (JP); Kazuhiko Yumikake, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 12/055,954

(22) Filed: Mar. 26, 2008

(65) Prior Publication Data

US 2008/0239238 A1    Oct. 2, 2008

(30) Foreign Application Priority Data

Mar. 30, 2007   (JP) ............................. 2007-095123

(51) Int. Cl.
*A61B 3/14* (2006.01)

(52) U.S. Cl. .................. 351/206; 351/205; 351/221

(58) Field of Classification Search ............... 351/205, 351/206, 209, 210, 211, 221, 246
See application file for complete search history.

(56) References Cited

U.S. PATENT DOCUMENTS

| | | | |
|---|---|---|---|
| 2006/0187462 | A1 | 8/2006 | Srinivasan et al. |
| 2006/0228011 | A1 | 10/2006 | Everett et al. |
| 2007/0285619 | A1* | 12/2007 | Aoki et al. ................ 351/206 |
| 2008/0159468 | A1* | 7/2008 | Chong ........................... 378/4 |

FOREIGN PATENT DOCUMENTS

| | | |
|---|---|---|
| JP | 11-325849 | 11/1999 |
| JP | 2002-139421 | 5/2002 |
| JP | 2003-000543 | 1/2003 |
| WO | WO-2006/058735 | 6/2006 |

OTHER PUBLICATIONS

M. Wojtkowski et al., "Three-dimensional Retinal Imaging with High-Speed Ultrahigh-Resolution Optical Coherence Tomography," Ophthalmology, Vo.112, No. 10, Oct. 2005, pp. 1734-1746.

* cited by examiner

*Primary Examiner*—Huy K Mai
(74) *Attorney, Agent, or Firm*—Edwards Angell Palmer & Dodge LLP

(57) ABSTRACT

An optical image measurement device comprises: an interference-light generator configured to generate an interference light by splitting a low-coherence light into a signal light and a reference light and superimposing the signal light having passed through an eye and the reference light having passed through a reference object; a detector configured to detect the generated interference light; a calculator configured to obtain intensity distribution of the interference light in the eye, based on a result of the detection by the detector; a determining part configured to determine a projection position of the signal light to the eye, based on the obtained intensity distribution; and an image forming part configured to form an image of the eye, based on a result of detection of a new interference light based on a new signal light projected toward the determined projection position and a new reference light having passed through the reference object.

17 Claims, 9 Drawing Sheets

OPTICAL IMAGE MEASUREMENT DEVICE AND OPTICAL IMAGE MEASUREMENT METHOD

BACKGROUND OF THE INVENTION

1. Field of the Invention

The present invention relates to an optical image measurement device and an optical image measurement method for forming an image of an eye by projecting a light beam to the eye and using a reflected light therefrom.

2. Description of the Related Art

In recent years, attention has been focused on an optical image measurement technique of forming an image showing the surface morphology or internal morphology of a measurement object by using a light beam from a laser light source or the like. Because this optical image measurement technique does not have invasiveness to human bodies unlike an X-ray CT device, it is expected to employ this technique particularly in the medical field.

Japanese Unexamined Patent Application Publication JP-A 11-325849 discloses an optical image measurement device configured in a manner that: a measuring arm scans an object by using a rotary deflection mirror (Galvano mirror); a reference mirror is disposed to a reference arm; at the outlet thereof, such an interferometer is used that the intensity of a light caused by interference of light fluxes from the measuring arm and the reference arm is analyzed by a spectrometer; and the reference arm is provided with a device gradually changing the light flux phase of the reference light in non-continuous values.

The optical image measurement device disclosed in JP-A 11-325849 uses a method of so-called "Fourier Domain OCT (Optical Coherence Tomography)." That is to say, the morphology of the measurement object in the depth direction (z-direction) is imaged by applying a beam of a low-coherence light to a measurement object, obtaining the spectrum intensity distribution of the reflected light, and subjecting the obtained distribution to Fourier transform.

Furthermore, the optical image measurement device described in JP-A 11-325849 is provided with a Galvano mirror scanning with a light beam (a signal light), thereby being capable of forming an image of a desired measurement region of a measurement object. Because this optical image measurement device scans with the light beam only in one direction (x-direction) orthogonal to the z-direction, a formed image is a 2-dimensional tomographic image in the depth direction (z-direction) along the scanning direction of the light beam (the x-direction).

Further, Japanese Unexamined Patent Application Publication JP-A 2002-139421 discloses a technique of scanning with a signal light in both the horizontal and vertical directions to thereby form a plurality of 2-dimensional tomographic images in the horizontal direction and, based on these plurality of tomographic images, acquiring and imaging 3-dimensional tomographic information of a measurement range. A method for 3-dimensional imaging is, for example, a method of arranging and displaying a plurality of tomographic images in the vertical direction (referred to as stack data or the like), and a method of forming a 3-dimensional image by subjecting a plurality of tomographic images to a rendering process.

Further, Japanese Unexamined Patent Application Publication JP-A 2003-000543 discloses a configuration of using such an optical image measurement device in the ophthalmic field.

Application of a conventional optical image measurement device in the ophthalmic field may cause problems as described below. First, in a conventional optical image measurement device, in a case where an eye has a site reducing the intensity of a signal light such as a nuclear cataract and a subcapsular cataract in the eye, the signal light is projected to a fundus oculi through this site. Therefore, the intensity of a fundus oculi reflection light of the signal light is decreased, and an interference light with sufficient intensity cannot be detected, with the result that a clear OCT image cannot be acquired. Moreover, the accuracy of an OCT image may decrease resulting from scatter of the signal light at this site.

It may be considered to previously specify such a site and perform position matching (alignment) of the eye with the device so that the signal light is projected avoiding this site. However, since such a preparation work requires a lot of effort, a load on the examiner increases. Moreover, since the examination takes more time, a load on the patient also increases. Especially in the case of performing plural times of measurement at a single site as in an observation of clinical course, it is necessary to perform alignment for every measurement, which is troublesome.

Further, in a conventional optical image measurement device, it is impossible to previously grasp what image will be acquired actually. Therefore, there is a case where measurement is performed in the insufficiently aligned condition and an image is acquired at a site displaced from an observation target such as an optic disk, a macula and a lesion. Consequently, it takes meaningless time and effort for measurement once more.

SUMMARY OF THE INVENTION

The present invention was made to solve such problems, and an object of the present invention is to provide a technique by which it is possible to easily acquire a clear OCT image even if an eye has a site reducing the intensity of a signal light.

Another object of the present invention is to provide a technique by which it is possible to prevent a case where a measurement is performed in the insufficiently aligned condition.

In order to achieve the aforementioned objects, in a first aspect of the present invention, an optical image measurement device comprises: an interference-light generator configured to generate an interference light by splitting a low-coherence light into a signal light and a reference light and superimposing the signal light having passed through an eye and the reference light having passed through a reference object; a detector configured to detect the generated interference light; a calculator configured to obtain intensity distribution of the interference light in the eye, based on a result of the detection by the detector; a determining part configured to determine a projection position of the signal light to the eye, based on the obtained intensity distribution; and an image forming part configured to form an image of the eye, based on a result of detection of a new interference light based on a new signal light projected toward the determined projection position and a new reference light having passed through the reference object.

In a second aspect of the present invention, an optical image measurement device comprises: an optical system configured to project a light to an eye and detect a light reflected by the eye; a calculator configured to obtain intensity distribution of the reflected light in the eye, based on a result of the detection by the optical system; a determining part configured to determine a projection position of a signal light to the eye, based on the obtained intensity distribution; an interference-light generator configured to generate an interference light by splitting a low-coherence light into a signal light and a reference light, projecting the signal light to the determined projection position, and superimposing the signal light having passed through the eye and the reference light having passed through a reference object; a detector configured to detect the generated interference light; and an image forming part configured to form an image of the eye, based on a result of the detection of the interference light.

In a third aspect of the present invention, an optical image measurement method comprises: generating an interference light by splitting a low-coherence light into a signal light and a reference light and superimposing the signal light having passed through an eye and the reference light having passed through a reference object; detecting the generated interference light; obtaining intensity distribution of the interference light in the eye based on a result of the detection; determining a projection position of the signal light to the eye, based on the obtained intensity distribution; projecting a new signal light based on a new low-coherence light toward the determined projection position; generating a new interference light by superimposing a new signal light having passed through the eye and a new reference light based on the new low-coherence light; detecting the generated new interference light; and forming an image of the eye, based on a result of the detection of the new interference light.

In a fourth aspect of the present invention, an optical image measurement method comprises: projecting a light to an eye and detecting a light reflected by the eye; obtaining intensity distribution of the reflected light in the eye based on a result of the detection; determining a projection position of a signal light to the eye, based on the obtained intensity distribution; generating an interference light by splitting a low-coherence light into a signal light and a reference light, projecting the signal light to the determined projection position, and superimposing the signal light having passed through the eye and the reference light having passed through a reference object; detecting the generated interference light; and forming an image of the eye based on a result of the detection of the interference light.

According to the present invention, it is possible to obtain the intensity distribution of an interference light based on the result of detection of the interference light; determine a projection position of a signal light to an eye based on this intensity distribution; and form an image of the eye based on the result of detection of a new interference light based on a new signal light projected toward the determined projection position of the signal light and a new reference light having passed through a reference object. Therefore, even if an eye has a site reducing the intensity of a signal light, it is possible to determine a projection position of the signal light so as to avoid the site, whereby it is possible to easily acquire a clear OCT image.

Further, according to the present invention, it is possible to previously grasp what image will be acquired actually, by forming an image based on an interference light acquired in a measurement for determining a projection position of a signal light. Therefore, it is possible to prevent a case where a measurement is performed in the insufficiently aligned condition.

Furthermore, according to the present invention, it is possible to obtain the intensity distribution of a reflected light based on the result of detection of the reflected light of a light projected to an eye; determine a projection position of a signal light to the eye based on this intensity distribution; and form an image of the eye based on the result of detection of an interference light generated by projecting the signal light to this projection position. Therefore, even if an eye has a site reducing the intensity of a signal light, it is possible to determine a projection position of the signal light so as to avoid the site, whereby it is possible to easily acquire a clear OCT image.

BRIEF DESCRIPTION OF THE DRAWINGS

FIG. 7A shows an example of the scanning pattern of the signal light when a fundus oculi is seen from the incident side of the signal light into an eye. FIG. 7B shows an example of an arrangement pattern of scanning points on each scanning line.

DETAILED DESCRIPTION OF THE PREFERRED EMBODIMENT

Figure 1:
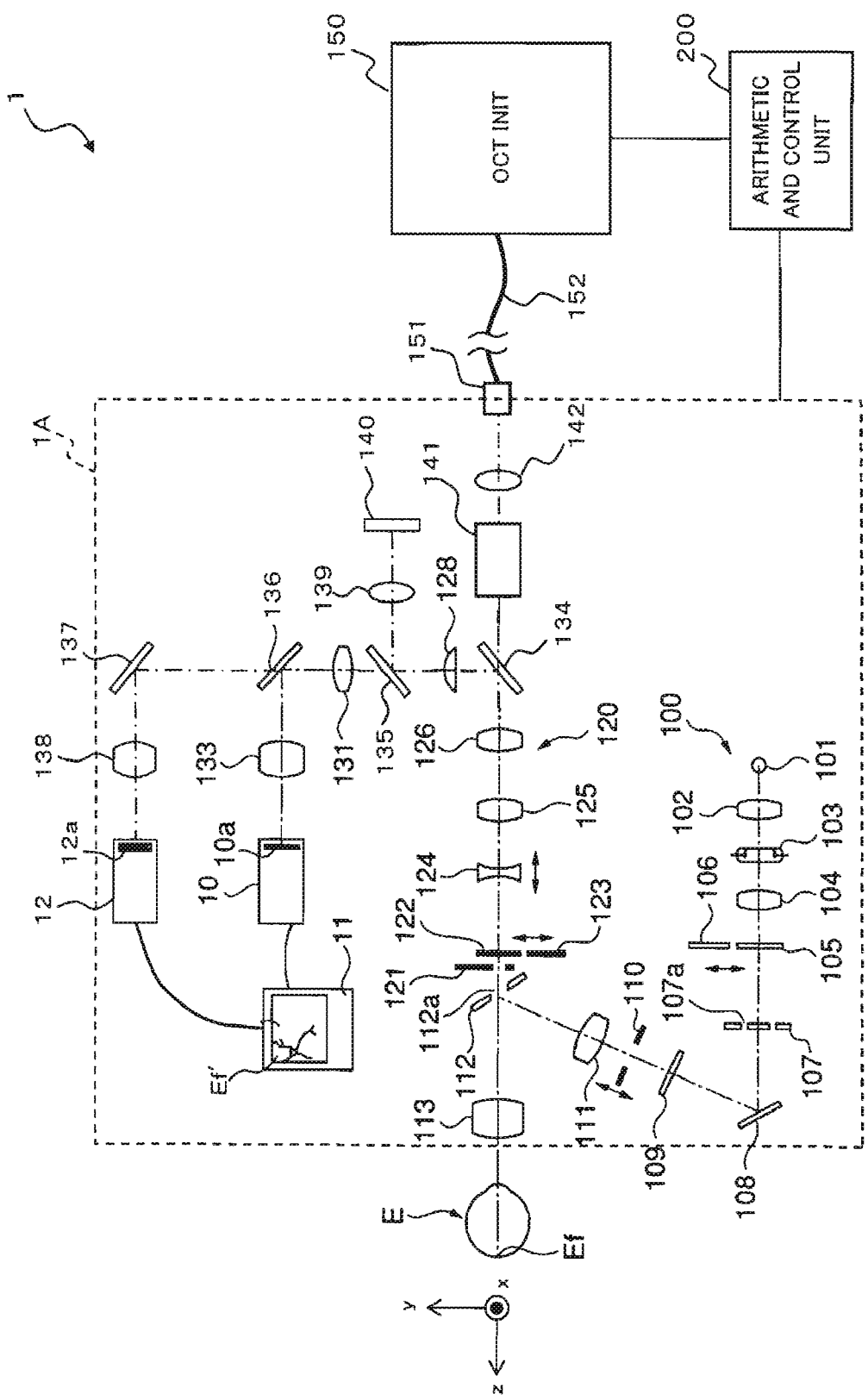
FIG. 1 is a schematic configuration diagram showing an example of the entire configuration in an embodiment of a fundus oculi observation device functioning as the optical image measurement device according to the present invention.

An example of a preferred embodiment of the optical image measurement device and the optical image measurement method according to the present invention will be described in detail referring to the drawings.

The present invention is applied to use in the ophthalmic field. The present invention makes it possible to easily acquire a clear OCT image by determining the projection position of a light beam (a signal light) suited to an eye before actually acquiring the image.

[Device Configuration]

Figure 2:
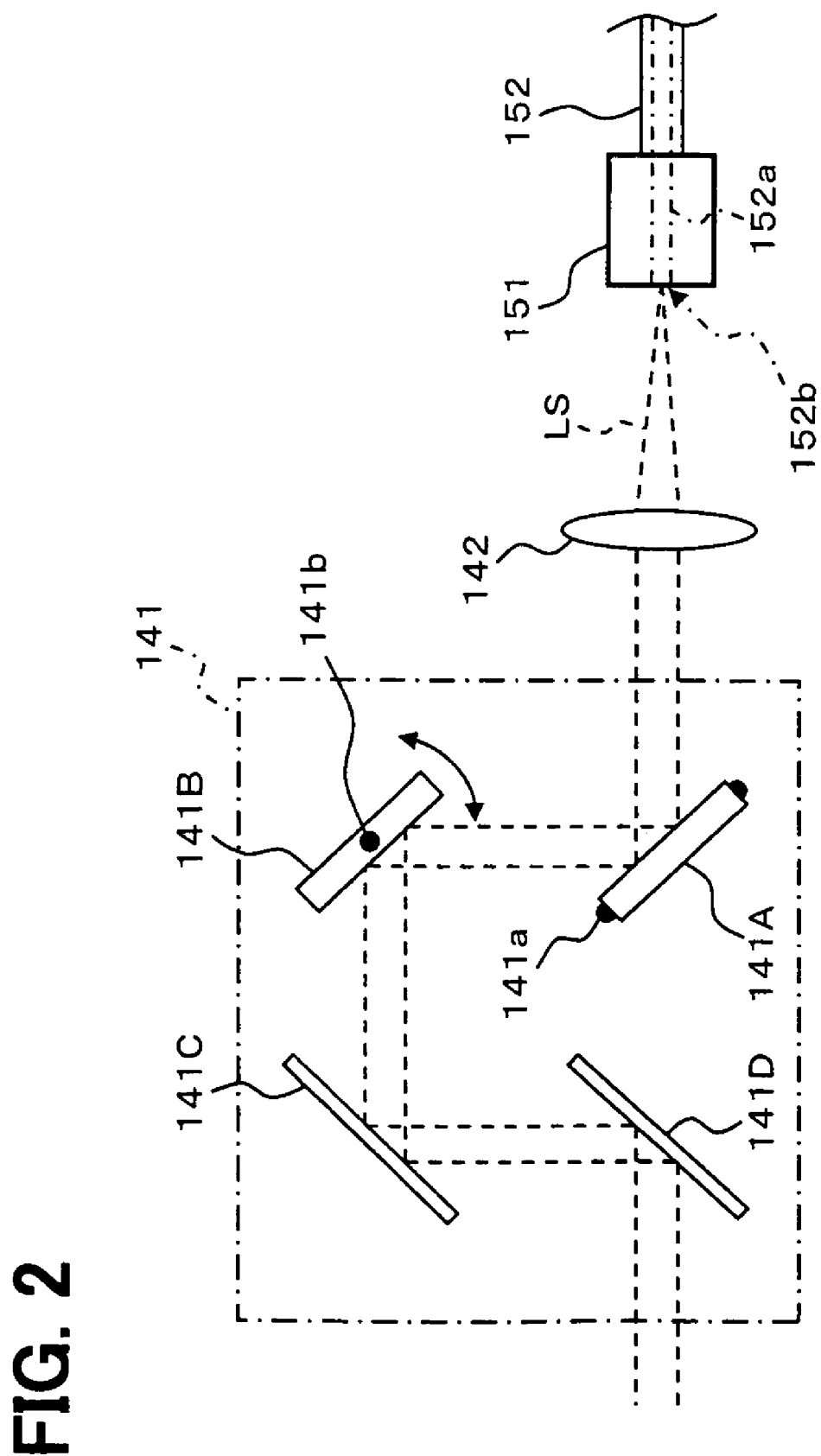
FIG. 2 is a schematic configuration diagram showing an example of the configuration of a scan unit installed in a retinal camera unit in the embodiment of the fundus oculi observation device functioning as the optical image measurement device according to the present invention.
Figure 3:
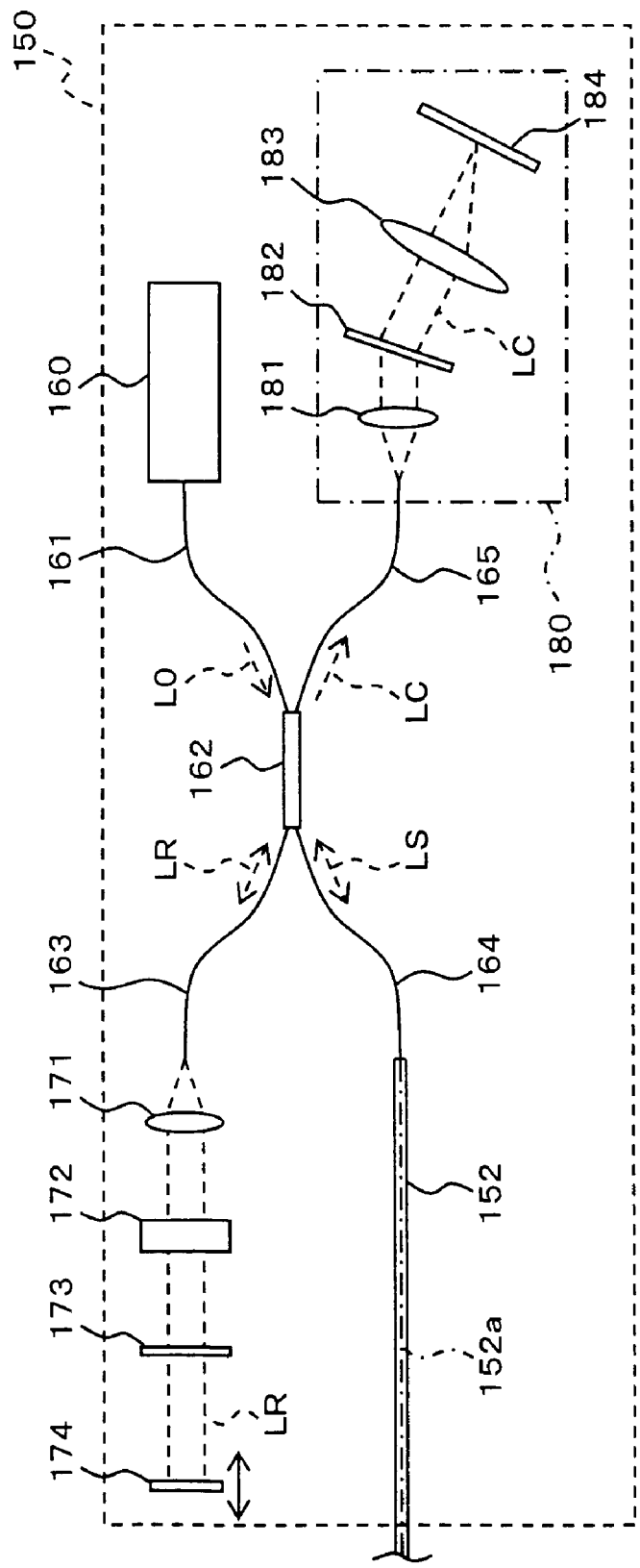
FIG. 3 is a schematic configuration diagram showing an example of the configuration of an OCT unit in the embodiment of the fundus oculi observation device functioning as the optical image measurement device according to the present invention.
Figure 4:
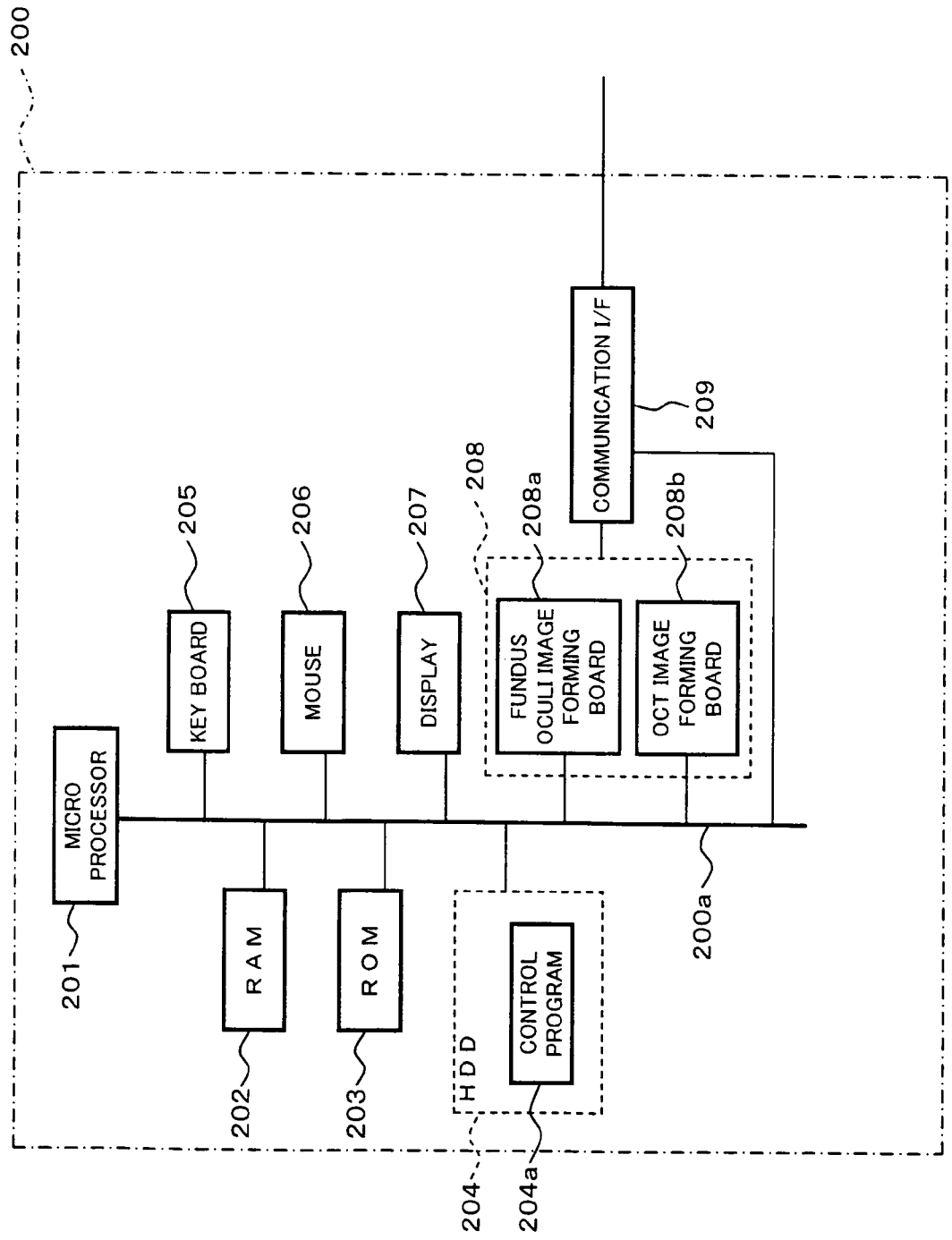
FIG. 4 is a schematic block diagram showing an example of the hardware configuration of an arithmetic and control unit in the embodiment of the fundus oculi observation device functioning as the optical image measurement device according to the present invention.
Figure 5:
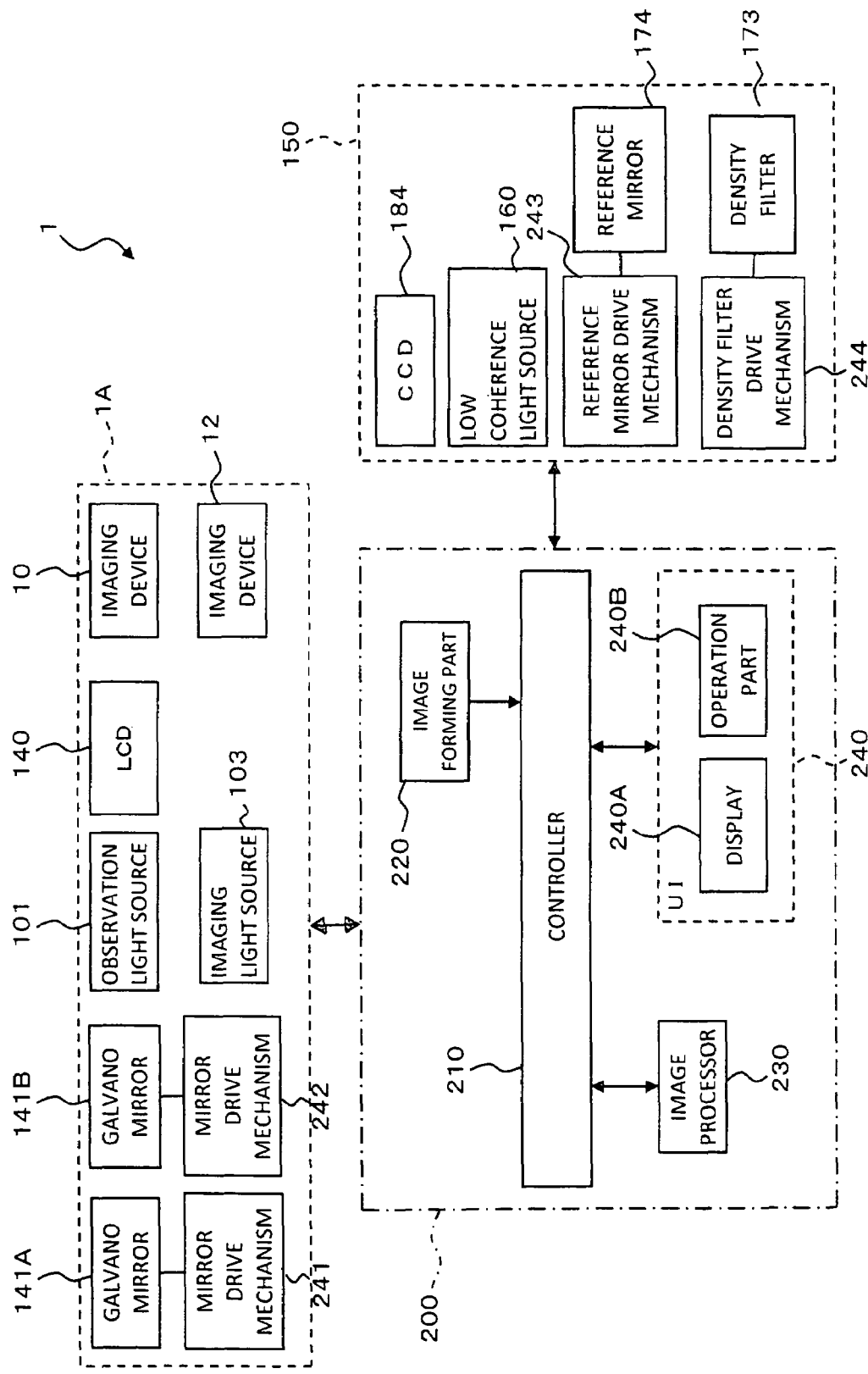
FIG. 5 is a schematic block diagram showing an example of the configuration of a control system in the embodiment of the fundus oculi observation device functioning as the optical image measurement device according to the present invention.
Figure 6:
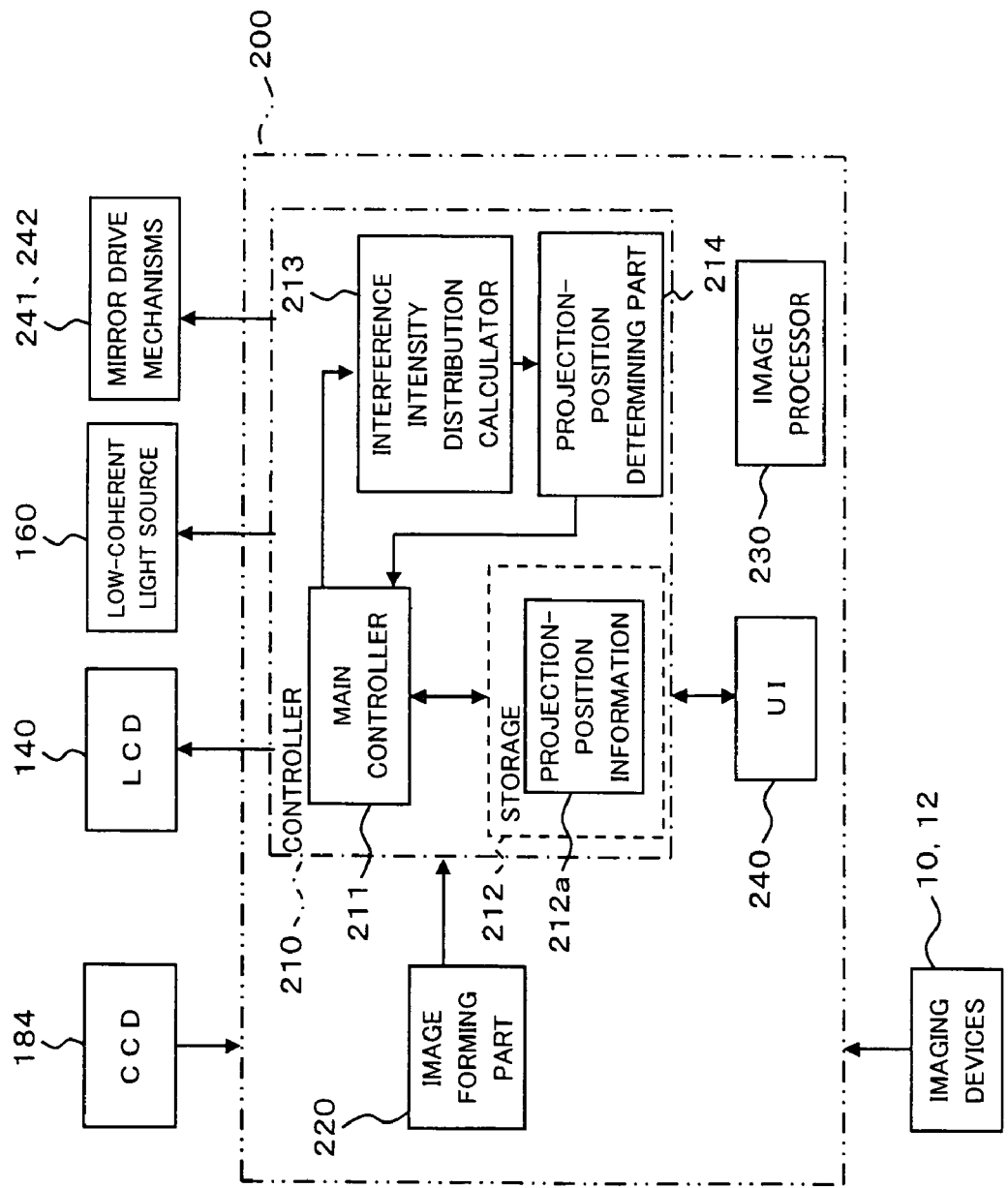
FIG. 6 is a schematic block diagram showing an example of the configuration of a control system in the embodiment of the fundus oculi observation device functioning as the optical image measurement device according to the present invention.

First, referring to FIGS. 1 to 6, the configuration in an embodiment of the optical image measurement device according to the present invention will be described. FIG. 1 shows an example of the entire configuration of a fundus oculi observation device 1 having a function as the optical image measurement device according to the present invention. FIG. 2 shows an example of the configuration of a scan unit 141 in a retinal camera unit 1A. FIG. 3 shows an example of the configuration of an OCT unit 150. FIG. 4 shows an example of the hardware configuration of an arithmetic and control unit 200. FIGS. 5 and 6 show an example of the configuration of a control system of the fundus oculi observation device 1.

[Entire Configuration]

The fundus oculi observation device 1 comprises the retinal camera unit 1A, the OCT unit 150 and the arithmetic and control unit 200 as shown in FIG. 1. The retinal camera unit 1A has almost the same optical system as the conventional retinal camera capturing a 2-dimensional image of the fundus oculi surface. The OCT unit 150 houses an optical system functioning as the optical image measurement device. The arithmetic and control unit 200 is equipped with a computer executing various kinds of arithmetic processes, control processes and so on.

To the OCT unit 150, one end of a connection line 152 is attached. A connector part 151 connecting the connection line 152 to the retinal camera unit 1A is attached to the other end of the connection line 152. A conductive optical fiber runs through inside the connection line 152. Thus, the OCT unit 150 and the retinal camera unit 1A are optically connected via the connection line 152.

[Configuration of Retinal Camera Unit]

The retinal camera unit 1A is used for forming a 2-dimensional image of the surface of a fundus oculi of an eye, based on optically acquired data (data detected by imaging devices 10 and 12). Here, the 2-dimensional image of the surface of the fundus oculi refers to a color image or monochrome image of the surface of the fundus oculi, a fluorescent image (a fluorescein angiography image, an indocyanine green fluorescent image, etc.), and the like. As well as the conventional retinal camera, the retinal camera unit 1A is provided with an illumination optical system 100 that illuminates a fundus oculi Ef, and an imaging optical system 120 that guides the fundus oculi reflection light of the illumination light to the imaging device 10.

Although the details will be described later, the imaging device 10 in the imaging optical system 120 detects an illumination light having a wavelength of a near-infrared region. Moreover, the imaging optical system 120 is further provided with the imaging device 12 detecting an illumination light having a wavelength of a visible region. Moreover, the imaging optical system 120 guides a signal light coming from the OCT unit 150 to the fundus oculi Ef, and guides the signal light having passed through the fundus oculi Ef to the OCT unit 150.

The illumination optical system 100 includes: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 outputs an illumination light having a wavelength of a visible region included in a range of about 400 nm to 700 nm, for example. Moreover, the imaging light source 103 outputs an illumination light having a wavelength of a near-infrared region included in a range of about 700 nm to 800 nm, for example. The near-infrared light outputted from the imaging light source 103 is set so as to have a shorter wavelength than the light used by the OCT unit 150 (described later).

Further, the imaging optical system 120 includes: the objective lens 113; the aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

The dichroic mirror 134 is configured to reflect the fundus oculi reflection light (having a wavelength included in the range of about 400 nm to 800 nm) of the illumination light from the illumination optical system 100, and to transmit a signal light LS (having a wavelength included in the range of, for example, about 800 nm to 900 nm; described later) from the OCT unit 150. Further, the dichroic mirror 136 is configured to transmit the illumination light having a wavelength of the visible region from the illumination optical system 100 (a visible light having a wavelength of about 400 nm to 700 nm outputted from the observation light source 101), and to reflect the illumination light having a wavelength of the near-infrared region (a near-infrared light having a wavelength of about 700 nm to 800 nm outputted from the imaging light source 103).

On the LCD 140, a fixation target (an internal fixation target) or the like for fixing the eye E is displayed. A light from the LCD 140 is reflected by the half mirror 135 after being converged by the lens 139, and is reflected by the dichroic mirror 136 after having passed through the field lens 128. Furthermore, this light passes through the imaging lens 126, the relay lens 125, the variable magnifying lens 124, the aperture mirror 112 (the aperture 112a thereof), the objective lens 113 and so on, and enters into the eye E. Consequently, the internal fixation target is projected on the fundus oculi Ef of the eye E.

The LCD 140 and the optical elements for projecting the internal fixation target onto the fundus oculi Ef are examples of the "presenting part" in the present invention. Here, the LCD 140 is an example of the "fixation-target display" configured to display a fixation target, and the abovementioned optical elements are examples of the "projection optical system" configured to project the displayed fixation target onto a fundus oculi. Furthermore, the "presenting part" configured to present the fixation target to the eye E is an example of the "changing part" in the present invention.

The image pick-up element 10a is an image pick-up element such as a CCD (Charge Coupled Device) and a CMOS (Complementary Metal Oxide Semiconductor) installed in the imaging device 10 such as a TV camera, and detects particularly a light having a wavelength of the near-infrared region. In other words, the imaging device 10 is an infrared TV camera that detects a near-infrared light. The imaging device 10 outputs video signals as a result of detection of the near-infrared light.

A touch panel monitor 11 displays a 2-dimensional image of the surface of the fundus oculi Ef (the fundus oculi image Ef'), based on these video signals. Moreover, these video signals are sent to the arithmetic and control unit 200, and a fundus oculi image is displayed on the display (described later).

For imaging a fundus oculi by the imaging device 10, for example, an illumination light outputted from the imaging light source 103 of the illumination optical system 100 and having a wavelength of the near-infrared region is used.

On the other hand, the image pick-up element 12*a* is an image pick-up element such as a CCD and a CMOS installed in the imaging device 12 such as a TV camera, and particularly detects a light having a wavelength of the visible region. That is, the imaging device 12 is a TV camera detecting a visible light. The imaging device 12 outputs video signals as a result of detection of the visible light.

The touch panel monitor 11 displays a 2-dimensional image of the surface of the fundus oculi Ef (the fundus oculi image Ef), based on these video signals. Moreover, these video signals are sent to the arithmetic and control unit 200, and a fundus oculi image is displayed on the display (described later).

For imaging a fundus oculi by the imaging device 12, for example, an illumination light outputted from the observation light source 101 of the illumination optical system 100 and having a wavelength of the visible region is used.

The retinal camera unit 1A is provided with a scan unit 141 and a lens 142. The scan unit 141 includes a component for scanning a projection position on the fundus oculi Ef with a light outputted from the OCT unit 150 (the signal light LS; described later).

The lens 142 makes the signal light LS guided from the OCT unit 150 through the connection line 152 enter into the scan unit 141 in the form of a parallel light flux. Moreover, the lens 142 converges the fundus oculi reflection light of the signal light LS having passed through the scan unit 141.

FIG. 2 shows an example of the configuration of the scan unit 141. The scan unit 141 includes Galvano mirrors 141A and 141B, and reflection mirrors 141C and 141D.

The Galvano mirrors 141A and 141B are reflection mirrors disposed so as to be rotatable about rotary shafts 141*a* and 141*b*, respectively. The Galvano mirrors 141A and 141B are rotated about the rotary shafts 141*a* and 141*b*, respectively, by a drive mechanism described later (mirror drive mechanisms 241 and 242 shown in FIG. 5). Consequently, the reflection faces (faces reflecting the signal light LS) of the Galvano mirrors 141A and 141B are turned around, respectively.

The rotary shafts 141*a* and 141*b* are arranged orthogonally to each other. In FIG. 2, the rotary shaft 141*a* of the Galvano mirror 141A is arranged in parallel to the paper face. On the other hand, the rotary shaft 141*b* of the Galvano mirror 141B is arranged in the orthogonal direction to the paper face. That is to say, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the Galvano mirrors 141A and 141B act so as to turn directions of reflecting the signal light LS into directions orthogonal to each other. As seen from FIGS. 1 and 2, scan with the signal light LS is performed in the x-direction when the Galvano mirror 141A is rotated, and scan with the signal light LS is performed in the y-direction when the Galvano mirror 141B is rotated.

The signal lights LS reflected by the Galvano mirrors 141A and 141B are reflected by reflection mirrors 141C and 141D, thereby traveling in the same direction as having entered into the Galvano mirror 141A.

An end face 152*b* of the optical fiber 152*a* inside the connection line 152 is arranged facing the lens 142. The signal light LS emitted from the end face 152*b* travels expanding its beam diameter toward the lens 142, and is converged to a parallel light flux by the lens 142. On the contrary, the signal light LS having passed through the fundus oculi Ef is converged toward the end face 152*b* by the lens 142, and enters into the optical fiber 152*a*.

[Configuration of OCT Unit]

Next, the configuration of the OCT unit 150 will be described referring to FIG. 3. The OCT unit 150 is a device for forming a tomographic image of a fundus oculi based on optically obtained data (data detected by a CCD 184 described later).

The OCT unit 150 has almost the same optical system as the conventional optical image measurement device. That is to say, the OCT unit 150 splits a low-coherence light into a reference light and a signal light and superimposes the signal light having passed through an eye with the reference light having passed through a reference object, thereby generating and detecting an interference light. The result of this detection (a detection signal) is inputted to the arithmetic and control unit 200. The arithmetic and control unit 200 forms a tomographic image of the eye by analyzing the detection signal.

A low-coherence light source 160 is composed of a broadband light source, such as a super luminescent diode (SLD) and a light emitting diode (LED), which outputs a low-coherence light L0. The low-coherence light L0 is, for example, a light including a light with a wavelength of the near-infrared region and having a temporal coherence length of approximately several tens of micrometers.

The low-coherence light L0 has a longer wavelength than the illumination light of the retinal camera unit 1A (wavelength of about 400 nm to 800 nm), for example, a wavelength included in a range of about 800 nm to 900 nm.

The low-coherence light L0 outputted from the low-coherence light source 160 is guided to an optical coupler 162 through an optical fiber 161. The optical fiber 161 is composed of, for example, a single mode fiber or a PM (Polarization maintaining) fiber. The optical coupler 162 splits this low-coherence light L0 into a reference light LR and the signal light LS.

Although the optical coupler 162 acts as both a part (splitter) for splitting a light and a part (coupler) for superimposing lights, it will be herein referred to as an "optical coupler" idiomatically.

The reference light LR generated by the optical coupler 162 is guided by an optical fiber 163 composed of a single mode fiber or the like, and emitted from the end face of the fiber. Furthermore, the reference light LR is converged to a parallel light flux by a collimator lens 171, passed through a glass block 172 and a density filter 173, and reflected by a reference mirror 174. The reference mirror 174 is an example of the "reference object" of the invention.

The reference light LR reflected by the reference mirror 174 is passed through the density filter 173 and the glass block 172, converged to the fiber end face of the optical fiber 163 by the collimator lens 171 again, and guided to the optical coupler 162 through the optical fiber 163.

Here, the glass block 172 and the density filter 173 act as a delaying part for matching the optical path lengths (optical distances) of the reference light LR and the signal light LS, and also as a dispersion compensation part for matching the dispersion characteristics of the reference light LR and the signal light LS.

Further, the density filter 173 also acts as a dark filter that reduces the amount of the reference light, and is composed of a rotating ND (neutral density) filter, for example. The density filter 173 acts so as to change the reduction amount of the reference light LR by being rotary driven by a drive mechanism including a drive unit such as a motor (a density filter drive mechanism 244 described later; refer to FIG. 5). Consequently, it is possible to change the amount of the reference light LR contributing to generation of an interference light LC.

Further, the reference mirror 174 is configured to move in the traveling direction of the reference light LR (the direction of the arrow pointing both sides shown in FIG. 3). With this, it is possible to ensure the optical path length of the reference light LR according to the axial length of the eye E, the working distance (the distance between the objective lens 113 and the eye E), etc. Moreover, it is possible to capture an image of any depth position of the fundus oculi Ef, by moving the reference mirror 174. The reference mirror 174 is moved by a drive mechanism (a reference mirror drive mechanism 243 described later; refer to FIG. 5) including a driver such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152. Here, the optical fiber 164 and the optical fiber 152a may be composed of one optical fiber, or may be integrally formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A. Furthermore, the signal light LS is projected to the eye E through the lens 142, the scan unit 141, the dichroic mirror 134, the imaging lens 126, the relay lens 125, the variable magnifying lens 124, the imaging diaphragm 121, the aperture 112a of the aperture mirror 112 and the objective lens 113. The barrier filter 122 and 123 are retracted from the optical path in advance, respectively, when the signal light LS is projected to the eye E.

The signal light LS having entered into the eye E forms an image on the fundus oculi Ef and is then reflected. At this moment, the signal light LS is not only reflected on the surface of the fundus oculi Ef, but also scattered at the refractive index boundary after reaching the deep area of the fundus oculi Ef. Therefore, the signal light LS having passed through the fundus oculi Ef contains information reflecting the morphology of the surface of the fundus oculi Ef and information reflecting the state of backscatter at the refractive index boundary of the deep area tissue of the fundus oculi Ef. This light may be simply referred to as the "fundus oculi reflection light of the signal light LS."

The fundus oculi reflection light of the signal light LS travels reversely along the abovementioned path within the retinal camera unit 1A, and is converged to the end face 152b of the optical fiber 152a. The, the signal light LS enters into the OCT unit 150 through the optical fiber 152a, and returns to the optical coupler 162 through the optical fiber 164.

The optical coupler 162 superimposes the signal light LS having returned through the eye E and the reference light LR reflected by the reference mirror 174, thereby generating the interference light LC. The generated interference light LC is guided into a spectrometer 180 through an optical fiber 165 composed of a single mode fiber or the like.

Although a Michelson-type interferometer is adopted in this embodiment, it is possible to properly employ, for instance, a Mach Zender type, etc. and any type of interferometer.

The interference-light generator" of the present invention comprises, for example, an optical coupler 162, an optical member on the optical path of the signal light LS (i.e., an optical member placed between the optical coupler 162 and the eye E), and an optical member on the optical path of the reference light LR (i.e., an optical member placed between the optical coupler 162 and the reference mirror 174), and specifically, comprises an interferometer equipped with the optical coupler 162, the optical fibers 163 and 164, and the reference mirror 174.

The spectrometer 180 comprises a collimator lens 181, a diffraction grating 182, an image-forming lens 183, and a CCD 184. The diffraction grating 182 may be a transmission-type diffraction grating that transmits light, or may be a reflection-type diffraction grating that reflects light. Moreover, it is also possible to use, instead of the CCD 184, another photodetecting element such as a CMOS. The interference light LC having entered into the spectrometer 180 is split (resolved into spectra) by the diffraction grating 182 after converged to a parallel light flux by the collimator lens 181. The split interference light LC is formed into an image on the image pick-up face of the CCD 184 by the image-forming lens 183. The CCD 184 detects the respective spectra of the split interference light LC and converts to electrical detection signals, and outputs the detection signals to the arithmetic and control unit 200. The CCD 184 is an example of the "detector" of the present invention.

[Configuration of Arithmetic and Control Unit]

Next, the configuration of the arithmetic and control unit 200 will be described. The arithmetic and control unit 200 analyzes detection signals inputted from the CCD 184 of the OCT unit 150, and forms a tomographic image of the fundus oculi Ef. The analysis method here is the same as the conventional Fourier Domain OCT method.

Further, the arithmetic and control unit 200 forms a 2-dimensional image showing the morphology of the surface of the fundus oculi Ef, based on the video signals outputted from the imaging devices 10 and 12 of the retinal camera unit 1A.

Furthermore, the arithmetic and control unit 200 controls each part of the retinal camera unit 1A and the OCT unit 150.

As control of the retinal camera unit 1A, the arithmetic and control unit 200 executes, for example: control of output of the illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of movement of the illumination diaphragm 110 (control of the diaphragm value); control of the diaphragm value of the imaging diaphragm 121; and control of movement of the variable magnifying lens 124 (control of the magnification). Moreover, the arithmetic and control unit 200 executes control of the operation of the Galvano mirrors 141A and 141B.

Further, as control of the OCT unit 150, the arithmetic and control unit 200 executes, for example: control of output of the low-coherence light L0 by the low-coherence light source 160; control of movement of the reference mirror 174; control of the rotary operation of the density filter 173 (the operation of changing the reduction amount of the reference light LR); and control of the accumulation time of the CCD 184.

The hardware configuration of the arithmetic and control unit 200 will be described referring to FIG. 4.

The arithmetic and control unit 200 is provided with a similar hardware configuration to that of a conventional computer. To be specific, the arithmetic and control unit 200 comprises: a microprocessor 201, a RAM202, a ROM203, a hard disk drive (HDD) 204, a keyboard 205, a mouse 206, a display 207, an image-forming board 208, and a communication interface (I/F) 209. These parts are connected via a bus 200a.

The microprocessor 201 includes a CPU (Central Processing Unit), an MPU (Micro Processing Unit) or the like. The microprocessor 201 executes operations characteristic to this embodiment, by loading a control program 204a stored in the hard disk drive 204, onto the RAM 202.

Further, the microprocessor 201 executes control of each part of the device described above, various arithmetic processes, etc. Moreover, the microprocessor 201 receives an operation signal from the keyboard 205 or the mouse 206, and executes control of each part of the device in response to the operation content. Furthermore, the microprocessor 201 executes control of a display process by the display 207, control of a transmission/reception process of data and signals by the communication interface 209.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is a display device such as an LCD and a CRT (Cathode Ray Tube) display, and displays various images like the fundus oculi Ef formed by the fundus oculi observation device 1, or displays various screens such as an operation screen and a set-up screen.

The user interface of the fundus oculi observation device 1 is not limited to the above configuration, and may include a track ball, a control lever, a touch panel type of LCD, a control panel for ophthalmology examinations, etc. As a user interface, it is possible to employ any configuration having a function of displaying and outputting information and a function of inputting information and operating the device.

The image-forming board 208 is a dedicated electronic circuit for forming (image data of) images of the fundus oculi Ef. The image-forming board 208 is provided with a fundus oculi image forming board 208a and an OCT image forming board 208b.

The fundus oculi image forming board 208a is a dedicated electronic circuit that forms image data of fundus oculi images based on the video signals from the imaging device 10 and the imaging device 12.

Further, the OCT image forming board 208b is a dedicated electronic circuit that forms image data of tomographic images of the fundus oculi Ef, based on the detection signals from the CCD 184 of the OCT unit 150.

By providing the image-forming board 208, it is possible to increase the processing speed of a process for forming fundus oculi images and tomographic images.

The communication interface 209 sends control signals from the microprocessor 201, to the retinal camera unit 1A or the OCT unit 150. Moreover, the communication interface 209 receives video signals from the imaging devices 10 and 12 or detection signals from the CCD 184 of the OCT unit 150, and inputs the signals to the image-forming board 208. At this moment, the communication interface 209 operates to input the video signals from the imaging devices 10 and 12, to the fundus oculi image forming board 208a, and input the detection signals from the CCD 184, to the OCT image forming board 208b.

Further, in a case where the arithmetic and control unit 200 is connected to a communication network such as a LAN (Local Area Network) and the Internet, it is possible to configure to be capable of data communication via the communication network, by providing the communication interface 209 with a network adapter like a LAN card or communication equipment like a modem. In this case, by mounting a server accommodating the control program 204a on the communication network, and at the same time, configuring the arithmetic and control unit 200 as a client terminal of the server, it is possible to operate the fundus oculi observation device 1.

[Configuration of Control System]

Next, the configuration of the control system of the fundus oculi observation device 1 will be described referring to FIGS. 5 and 6.

(Controller)

The control system of the fundus oculi observation device 1 is configured mainly having a controller 210 of the arithmetic and control unit 200. The controller 210 includes the microprocessor 201, the RAM202, the ROM203, the hard disk drive 204 (the control program 204a), and the communication interface 209.

The controller 210 executes the aforementioned control with the microprocessor 201 operating based on the control program 204a. The controller 210 is provided with a main controller 211, a storage 212, an interference intensity distribution calculator 213, and a projection-position determining part 214.

The main controller 211 controls the mirror drive mechanisms 241 and 242 to regulate the positions of the Galvano mirrors 141A and 141B, thereby performing scan the projection position of the signal light LS on the fundus oculi Ef. Further, the main controller 211 controls the LCD 140 to display the internal fixation target.

Further, the main controller 211 executes control of the low-coherence light source 160 and the CCD 184, control of the density filter drive mechanism 244 for rotating the density filter 173, control of the reference-mirror drive mechanism 243 for moving the reference mirror 174 in the traveling direction of the reference light LR, etc.

Further, the main controller 211 causes the display 240A of the user interface (UI) 240 to display two kinds of images captured by the fundus oculi observation device 1: that is, the fundus oculi image Ef' and a tomographic image. These images may be displayed on the display 240A separately, or may be displayed side by side.

The storage 212 stores projection-position information 212a. The projection-position information 212a is information indicating the projection position of the signal light LS, and is generated by the projection-position determining part 214. This generating process will be described later.

Further, the storage 212 stores various kinds of data, such as image data formed by an image forming part 220. A process of writing the data into the storage 212 and a process of reading out the data from the storage 212 are executed by the main controller 211.

The interference intensity distribution calculator 213 obtains the intensity distribution of the interference light LC based on the result of detection by the CCD 184. This process will be described more specifically. This process is executed as a preparation for acquisition of an OCT image of the fundus oculi Ef.

In the preparation work, first, the eye E is placed at a measurement position (a position facing the objective lens 113) and aligned as usual. Next, the main controller 211 controls the low coherence light source 160 and the mirror drive mechanisms 241 and 242 to scan with the signal light LS on the eye E. The CCD 184 detects the interference light LC consecutively generated by the scan. Each detection signal is inputted into the arithmetic and control device 200, and then into the interference intensity distribution calculator 213 by the main controller 211.

Each detection signal contains information on the intensity of the interference light LC (i.e., the interference intensity) corresponding to the projection position of the signal light LS. The interference intensity distribution calculator 213 forms a map by associating the projection position of the signal light LS with the interference intensity, thereby obtaining the intensity distribution of the interference light. The intensity distribution of the interference light is information indicating the distribution of the interference intensity within a scanning region (e.g., a scanning region R described later) of the signal light LS.

The projection position of the signal light LS can be obtained from, for example, the positions (the directions of the reflection faces) of the Galvano mirrors 141A and 141B at the time of projection of the signal light LS onto the projection position. The obtained intensity distribution of the interference light is inputted into the projection-position determining part 214.

The interference intensity distribution calculator 213 functioning as described above is an example of the "calculator" in the present invention.

The projection-position determining part 214 determines the projection position of the signal light LS to the eye E based on the intensity distribution of the interference light obtained by the interference intensity distribution calculator 213. A specific example of this process will be described.

The projection-position determining part 214 specifies a region (a target region) whose intensity is equal to or less than a specific threshold value, in the interference intensity distribution. This threshold value may be a default value previously set, or may be set for every measurement.

In an example of a process of setting the threshold value for every measurement, a histogram for every intensity (or for every intensity range) is created by analyzing the intensity distribution of the interference light. This histogram represents the frequencies of each intensity (or each intensity range). The threshold value can be set based on the frequencies of each intensity in the histogram.

Further, it is also possible to extract a portion with an extremely small intensity and set the threshold value so as to separate this portion from another portion in this histogram.

The projection-position determining part 214 sets the projection position of the signal light LS within a region other than the target region specified in this way. At this moment, the entire region other than the target region may be set as the projection position, or only part thereof may be set as the projection position. In the latter case, for example, it is possible to set the projection position so as to avoid the vicinity of the target region.

Another operation pattern of the projection-position determining part 214 will be described. In contrast to the above example, the projection-position determining part 214 specifies a region with a larger intensity than a specific threshold value in the intensity distribution of the interference light and sets the projection position of the signal light LS within the specified region. This threshold value can be set in a similar way as in the above example. Further, the entire specified region may be set as the projection position, or only part thereof may be set as the projection position.

The projection-position determining part 214 functioning in this way is an example of the "determining part" in the present invention.

The projection-position determining part 214 sends information on the determined projection position of the signal light LS to the main controller 211. The main controller 211 causes the storage 212 to store this information as the projection-position information 212a. The projection-position information 212a may be, for example, information indicating the positions (directions) of the Galvano mirrors 141A and 141B, or may be coordinate values in the x-y coordinate system shown in FIG. 1.

(Image Forming Part)

The image forming part 220 forms image data of the fundus oculi image Ef based on the video signals from the imaging devices 10 and 12. Moreover, the image forming part 220 forms image data of the tomographic image of the fundus oculi Ef based on the detection signals from the CCD 184 of the OCT unit 150.

The imaging forming part 220 includes the image-forming board 208, the communication interface 209, and so on. In this specification, "image" may be identified with "image data" corresponding thereto.

(Image Processor)

The image processor 230 applies various kinds of image processing and analysis processes to image data of images formed by the image forming part 220. For example, the image processor 230 executes various kinds of correction processes such as brightness correction and dispersion correction of the images.

Further, the image processor 230 applies an interpolation process of interpolating pixels between tomographic images formed by the image forming part 220 to the tomographic images, thereby forming image data of a 3-dimensional image of the fundus oculi Ef.

Herein, image data of a 3-dimensional image is image data made by assigning pixel values to each of a plurality of voxels arranged 3-dimensionally, and is referred to as volume data, voxel data, or the like. In the case of displaying an image based on volume data, the image processor 230 applies a rendering process (such as volume rendering and MIP (Maximum Intensity Projection)) to this volume data, and forms image data of a pseudo 3-dimensional image seen from a specific view direction. On a display device such as the display 207, the pseudo 3-dimensional image based on the image data is displayed.

Further, the image processor 230 is also capable of forming stack data of a plurality of tomographic images. Stack data is image data that can be obtained by arranging a plurality of tomographic images acquired along a plurality of scanning lines based on the positional relationship of the scanning lines.

The image processor 230 operating as described above comprises the microprocessor 201, the RAM 202, the ROM 203, the hard disk drive 204 (control program 204a), etc.

The image forming part 220 and the image processor 230 are examples of the "image forming part" in the present invention.

(User Interface)

The user interface (UI) 240 is provided with the display 240A and an operation part 240B. The display 240A is composed of a display device such as the display 207. The operation part 240B is composed of an input device or operation device such as the keyboard 205 and the mouse 206.

[Signal Light Scanning and Image Processing]

Scan with the signal light LS is performed by turning around the reflecting surfaces of the Galvano mirrors 141A and 141B of the scan unit 141 as described before. The controller 210 controls the mirror drive mechanisms 241 and 242, respectively, to turn around the reflecting surfaces of the Galvano mirrors 141A and 141B, respectively, thereby scanning the fundus oculi Ef with the signal light LS.

When the reflecting surface of the Galvano mirror 141A is turned around, scan with the signal light LS in the horizontal direction (the x-direction in FIG. 1) is performed on the fundus oculi Ef. On the other hand, when the reflecting surface of the Galvano mirror 141B is turned around, scan with the signal light LS in the vertical direction (the y-direction in FIG. 1) is performed on the fundus oculi Ef. Further, by turning around both the reflecting surfaces of the Galvano mirrors 141A and 141B simultaneously, it is possible to scan with the signal light LS in the composed direction of the x-direction and y-direction. That is, by controlling these two Galvano mirrors 141A and 141B, it is possible to scan with the signal light LS in any direction on the x-y plane.

Figure 7A:
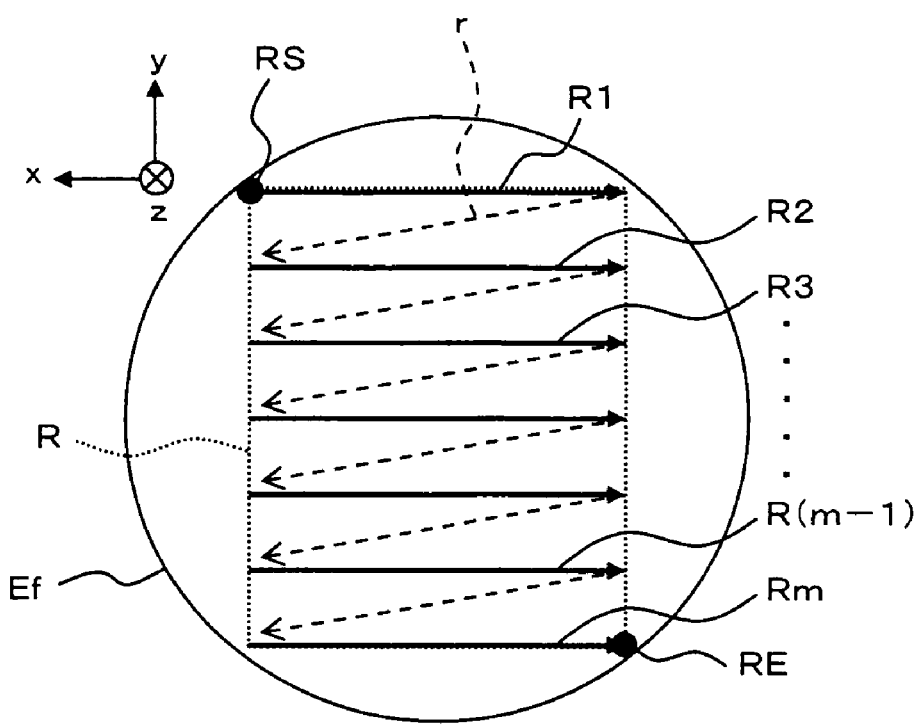
FIGS. 7A and 7B are schematic views showing an example of a scanning pattern of a signal light in the embodiment of the fundus oculi observation device functioning as the optical image measurement device according to the present invention.
Figure 7B:
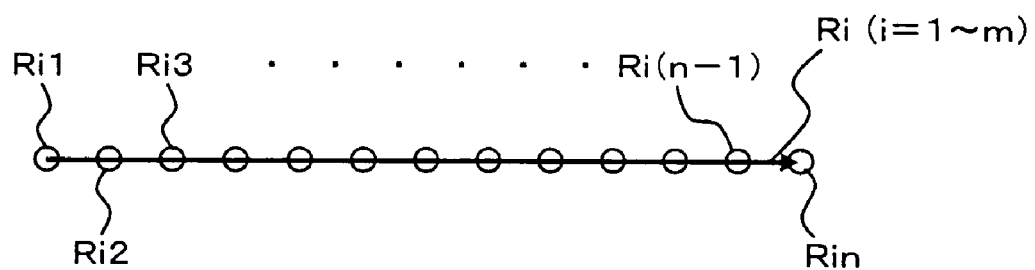

FIGS. 7A and 7B show an example of a scanning pattern of the signal light LS for forming an image of the fundus oculi Ef. FIG. 7A shows an example of the scanning pattern of the signal light LS when the fundus oculi Ef is seen from a direction in which the signal light LS enters the eye E (that is, seen from the −z side to the +z side in FIG. 1). Further, FIG. 7B shows an example of an arrangement pattern of scanning points (positions to perform image measurement) on each scanning line on the fundus oculi Ef.

As shown in FIG. 7A, scan with the signal light LS is performed within a rectangular scanning region R set in advance. Within the scanning region R, a plurality of (m number of) scanning lines R1 to Rm are set in the x-direction. When scan with the signal light LS is performed along each scanning line Ri (i=1 to m), a detection signal of the interference light LC is generated.

A direction of each scanning line Ri will be referred to as the "main scanning direction," and a direction orthogonal thereto will be referred to as the "sub-scanning direction." Accordingly, scan with the signal light LS in the main scanning direction is performed by turning around the reflecting surface of the Galvano mirror 141A. Scan in the sub-scanning direction is performed by turning around the reflecting surface of the Galvano mirror 141B.

On each scanning line Ri, as shown in FIG. 7B, a plurality of (n number of) scanning points Ri1 to Rin are set in advance.

In order to execute the scan shown in FIGS. 7A and 7B, the controller 210 firstly controls the Galvano mirrors 141A and 141B to set the entering target of the signal light LS into the fundus oculi Ef to a scan start position RS (a scanning point R11) on a first scanning line R1. Subsequently, the controller 210 controls the low-coherence light source 160 to flush the low-coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan with the signal light LS in the main scanning direction and set the entering target thereof to a scanning point R12, and causes the low-coherence light L0 to flush to make the signal light LS enter a scanning point R12. The CCD 184 receives the interference light LC based on the fundus oculi reflection light of this signal light LS at the scanning point R12, and outputs the detection signal to the controller 210.

In the same way, the controller 210 makes the low-coherence light L0 flush at each scanning point while moving the entering target of the signal light LS from a scanning point R13 to R14, ..., R1 (n−1) and R1n in order, thereby obtaining a detection signal outputted from the CCD 184 in response to the interference light LC for each scanning point.

When the measurement at the last scanning point R1n of the first scanning line R1 ends, the controller 210 controls the Galvano mirrors 141A and 141B simultaneously to move the entering target of the signal light LS to a first scanning point R21 of a second scanning line R2 along a line switching scan r. Then, by conducting the aforementioned measurement for each scanning point R2j (j=1 to n) of this second scanning line R2, a detection signal corresponding to each scanning point R2j is obtained.

In the same way, the measurement is performed for each of a third scanning line R3, ..., an m−1th scanning line R(m−1) and an mth scanning line Rm, whereby a detection signal corresponding to each scanning point is acquired. Symbol RE on the scanning line Rm is a scan end position corresponding to a scanning point Rmn.

As a result, the controller 210 obtains m×n number of detection signals corresponding to m×n number of scanning points Rij (i=1 to m, j=1 to n) within the scanning region R. Hereinafter, a detection signal corresponding to the scanning point Rij may be represented by Dij.

Interlocking control of movement of the scanning point and emission of the low-coherence light L0 as described above can be realized by synchronizing transmission timing of control signals to the mirror drive mechanisms 241 and 242 with transmission timing of a control signal to the low-coherence light source 160.

As described above, when causing each of the Galvano mirrors 141A and 141B to operate, the controller 210 stores the position of the scanning line Ri and the position of the scanning point Rij (coordinates on the x-y coordinate system) as information representing the content of the operation. This stored content (the scan position information) is used in an image forming process as conventional.

Next, an example of image processing in the case of scan with the signal light LS shown in FIGS. 7A and 7B will be described.

The image forming part 220 forms tomographic images of the fundus oculi Ef along each scanning line Ri (the main scanning direction). Further, the image processor 230 forms a 3-dimensional image of the fundus oculi Ef based on the tomographic images formed by the image forming part 220.

A process for forming tomographic images by the image forming part 220 includes a 2-step arithmetic process as conventional. In the first step of the arithmetic process, based on the detection signal Dij corresponding to each scanning point Rij, an image in the depth-wise direction (the z-direction in FIG. 1) of the fundus oculi Ef at the scanning point Rij is formed.

Figure 8:
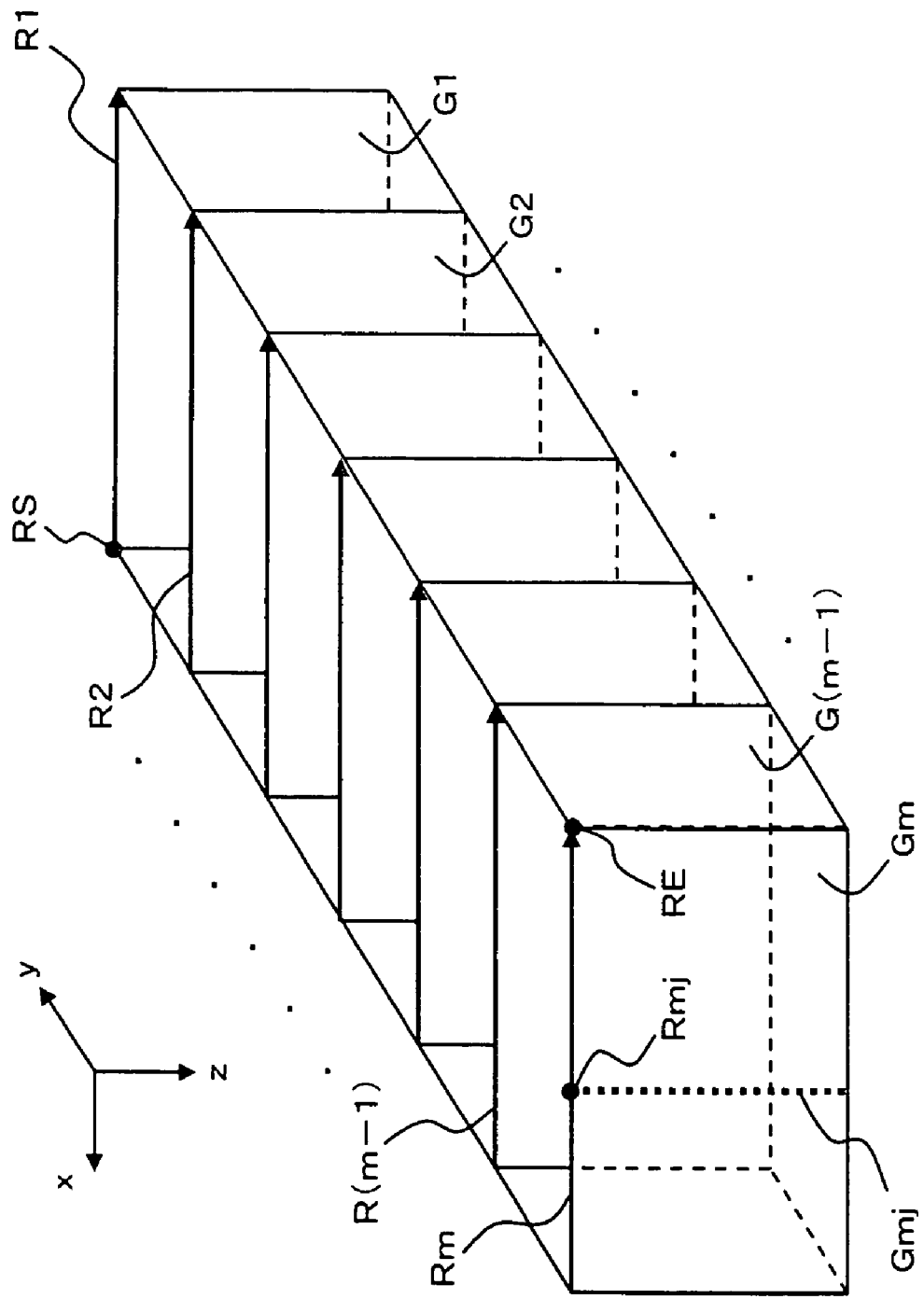
FIG. 8 is a schematic view showing an example of the scanning pattern of the signal light and a pattern of a tomographic image formed along each scanning line in the embodiment of the fundus oculi observation device functioning as the optical image measurement device according to the present invention.

FIG. 8 shows a pattern of tomographic images formed by the image forming part 220. In the second step of the arithmetic process, for each scanning line Ri, based on the depth-wise images at the n number of scanning points Ri1 to Rin, a tomographic image Gi of the fundus oculi Ef along the scanning line Ri is formed. At this moment, the image forming part 220 determines the arrangement and interval of the scanning points Ri1 to Rin by referring to the positional information (scan position information described before) of the scanning points Ri1 to Rin, and forms this scanning line Ri. Through the above process, it is possible to obtain m number of tomographic images G1 to Gm at different positions in the sub-scanning direction (y-direction).

Next, a process for forming a 3-dimensional image of the fundus oculi Ef by the image processor 230 will be explained. A 3-dimensional image of the fundus oculi Ef is formed based on the m number of tomographic images obtained through the abovementioned arithmetic process. The image processor 230 forms a 3-dimensional image of the fundus oculi Ef, for example, by performing a known interpolating process of interpolating an image between the adjacent tomographic images Gi and G (i+1).

At this moment, the image processor 230 determines the arrangement and interval of the scanning lines Ri by referring to the positional information of the scanning lines Ri, thereby forming a 3-dimensional image. For this 3-dimensional image, 3-dimensional coordinates (x, y, z) are set, based on the positional information of each scanning point Rij (the aforementioned scan position information) and the z coordinate in a depth-wise image.

Further, based on this 3-dimensional image, the image processor 230 can form a tomographic image of the fundus oculi Ef at a cross section in any direction other than the main scanning direction (x-direction). When the cross section is designated, the image processor 230 specifies the position of each scanning point (and/or an interpolated depth-wise image) on this designated cross section, extracts a depth-wise image at each of the specified positions (and/or an interpolated depth-wise image) from the 3-dimensional image, and arranges the plurality of extracted depth-wise images, thereby forming a tomographic image of the fundus oculi Ef at the designated cross section.

An image Gmj shown in FIG. 8 represents an image in the depth-wise direction (z-direction) at the scanning point Rmj on the scanning line Rm. In the same way, a depth-wise image at each scanning point Rij on the scanning line Ri formed in the aforementioned first-step arithmetic process is represented as the "image Gij."

[Usage Pattern]

Figure 9:
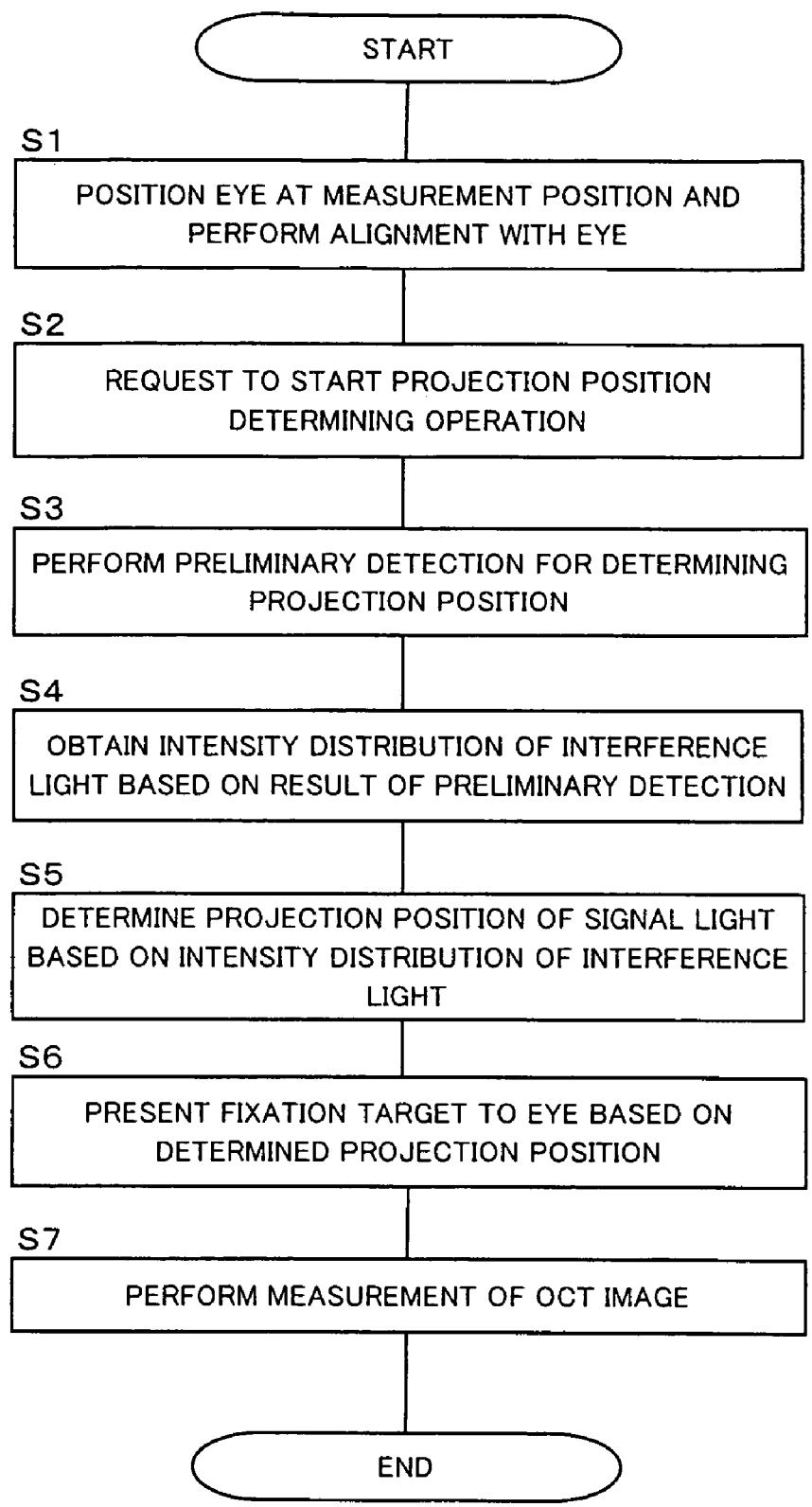
FIG. 9 is a flowchart showing an example of a usage pattern of the embodiment of the fundus oculi observation device functioning as the optical image measurement device according to the present invention.

A usage pattern of the fundus oculi observation device 1 will be described. A flowchart of FIG. 9 shows an example of this usage pattern.

First, the eye E is positioned at a specific measurement position (a position facing the objective lens 1113), and alignment with the eye E is performed (S1).

When the alignment is completed, the operator sends a request to start an operation for determining the projection position of the signal light LS by operating the operation part 240B (S2).

Upon receipt of the request, the main controller 211 controls the low coherence light source 160 and the mirror drive mechanisms 241 and 242 to scan with the signal light LS on the eye E (preliminary scan). The CCD 184 detects the interference lights LC consecutively generated in the preliminary scan, and inputs them into the arithmetic and control device 200. The series of operations will be referred to as "preliminary detection" (S3).

The interference intensity distribution calculator 213 obtains the intensity distribution of the interference light based on the detection signals acquired in the preliminary detection (S4).

Subsequently, the projection-position determining part 214 determines the projection position of the signal light LS on the eye E based on this intensity distribution of the interference light (S5). The determined projection position is stored in the storage 212 as the projection-position information 212a.

The main controller 211 controls the LCD 140 to display a fixation target for fixing the eye E so that the signal light LS is projected to the projection position shown in the projection-position information 212a, whereby this fixation target is presented to the eye E (S6). The eye E is fixed by staring at this fixation target.

A measurement of an OCT image is performed in a state in which the eye E is fixed (S7). That is, when the operator sends a request to start measurement of the OCT image from the operation part 240B, the main controller 211 having received the request controls the low coherence light source 160 and the mirror drive mechanisms 241 and 242 to conduct the measurement while scanning with the signal light LS, and the CCD 184 detects the interference light LS corresponding to each projection position of the signal light LS based on the projection-position information 212a and inputs each detected signal into the arithmetic and control device 200. The image forming part 220 and the image processor 230 form OCT images based on the detected signals. This is the end of description of this usage pattern.

[Actions and Advantageous Effects]

The fundus oculi observation device 1 obtains the intensity distribution of an interference light based on the result of detection of the interference light LC by the CCD 184, and determines the projection position of the signal light LS onto the eye E based on this intensity distribution. Then, an OCT image of the fundus oculi Ef is formed based on the detection result of a new interference light LC based on a new signal light LS projected toward the determined projection position and a new reference light LR having passed through the reference mirror 174.

Therefore, according to the fundus oculi observation device 1, in a case where the eye has a site reducing the intensity of the signal light LS, it is possible to determine the projection position of the signal light LS so as to avoid the site based on the intensity distribution of an interference light.

To be specific, according to the fundus oculi observation device 1, it is possible to fix the eye E so that the new signal light LS does not pass through the site, by presenting a fixation target to the eye E based on the determined projection position.

According to the fundus oculi observation device 1 acting as described above, even if the eye E has a site reducing the intensity of the signal light LS, it is possible to easily acquire a clear OCT image.

Further, according to the fundus oculi observation device 1, it is possible to form an OCT image based on the interference light LC acquired in the measurement for determining the projection position of the signal light LS. Consequently, it is possible to grasp in advance what image will actually be acquired, and it is possible to prevent a case where a measurement is conducted in the insufficiently aligned condition.

[Modification]

The configuration described above is merely an example for favorably implementing the present invention. Therefore, it is possible to properly make any modification within the scope and intent of the present invention.

The changing part related to the present invention is for changing the relative positions of the eye and the device so as to project a new signal light to the determined projection position of the signal light. In the above embodiment, the presenting part configured to present a fixation target to the eye functions as the changing part. However, the optical image measurement device according to the present invention may comprise the changing part other than the presenting part.

For example, it is possible to change the relative positions of the eye and the device (the case body of the optical system), by providing a stage for moving the device with respect to the eye. Although it is possible to move the eye with respect to the device by moving a jaw holder or a forehead rest, it is through to be desirable to configure to move the device, because there is a risk of increasing a burden on the subject such that the subject may feel uncomfortable.

A modification example will be described, which is particularly effective for acquisition of an OCT image at a single site (e.g., an optic disk, a macula, a lesion, etc.) of the fundus oculi Ef in a plurality of occasions as in an observation of clinical course or the like.

First, the main controller 211 causes the display 240A (the display) to display an OCT image having been acquired in the past. Here, the OCT image having been acquired in the past is stored in the storage 212. This OCT image does not need to be stored in a storage device within the arithmetic and control device 200, and may be archived in a storage device (a database) on a network such as a LAN within a hospital. Further, for example, the OCT image may be stored and archived in a storage medium such as a DVD-RAM so that they may be read out by using a drive device (not illustrated).

The operator observes the displayed OCT images, and designates a desired OCT image by operating the operation part 240B (the operating part). This designating operation can be conducted by, for example, clicking with the mouse 206.

The main controller 211 reads out the projection-position information 212a corresponding to the designated OCT image from the storage 212 (storing part). It is assumed that each of the projection-position information 212a is stored in the state associated with an OCT image in advance by identification information such as a patient ID, an examination ID, an image ID, or the like. This association process is conducted by, for example, the main controller 211. Upon controlled by the main controller 211, the changing part such as the LCD 140 changes the relative positions of the eye and the device based on the projection-position information 212a. Consequently, it is possible to project the signal light LS to (almost) the same position as in the designated past OCT image. Therefore, it is possible to easily acquire an OCT image at (almost) the same position as in the past OCT image.

For example, in a case where the OCT image is a tomographic image, the operator selects and designates a tomographic image in which a target site is favorably depicted from among past tomographic images. At this moment, the operator can select a tomographic image based on the position of a target site within the tomographic image. According to this modification, it is possible to easily acquire a tomographic image along (almost) the same scanning line as when the designated tomographic image has been acquired.

In this modification, the signal light LS is projected to the same projection position as in the image designated by the operator, but there is no limitation. For example, in a case where a past image to refer to is already decided, the operator does not need to designate. In this case, a projection position shown in the projection-position information corresponding to this past image is automatically set and scanned with the signal light.

The above embodiment describes a device capable of executing scan avoiding a site reducing the intensity of a signal light. However, even if a favorable image has been acquired, it is impossible to use the image for diagnosis in a case where, for example, a target site is not depicted or only part of the target site is depicted in the image. The following example may be applied in order to avoid such a situation.

When the projection position of the signal light LS is determined by the projection-position determining part 214, the controller 210 obtains the distance between the determined projection position and a specific reference position. This distance may indicate only a distance (a scalar quantity), or may indicate a distance and a direction (a vector quantity). Further, the reference position is a position set by, for example, the alignment conducted in Step 1 in the flowchart of FIG. 9.

In a case where the alignment is conducted with respect to a target site such as an optic disk, a macula and a lesion, the distance between the projection position and the reference position is equivalent to the distance from the projection position of the signal light LS to the target site. That is, the distance is information representing the positional relation between a target site and an OCT image to be acquired.

The controller 210 determines whether the distance between a projection position and a reference position is equal to or greater than a specific distance (for example, a preset distance). In the case of determining to be equal to or greater than the specific distance, the controller 210 causes the display 240A to display reporting information such as a message reporting the determination. The reporting information is not limited to such visual information, and may be auditory information and the like.

From the reporting information, the operator can recognize before measurement that an image at a position apart from the target site is to be acquired. Consequently, it is possible to avoid such inconvenience that the target site is not favorably depicted in the actually acquired image. The controller 210 and the display 240A are examples of the "reporting part" in the present invention.

Moreover, the controller 210 can cause the display 240A to display the distance obtained in the above manner, together with the OCT image formed by the image forming part 220. The operator can grasp the distance between the target site and the image, thereby determining whether the position of the image is proper.

In the above embodiment, the projection position of the signal light is determined based on the intensity distribution of the interference light based on the low-coherence light, but it is also possible to configure to determine the projection position of the signal light by using a different light. For example, in an optical image measurement device having a function of acquiring an OCT image and also a function of acquiring another type of image, it is possible to determine the projection position of a signal light by using a light for acquiring the other type of image.

An example will be described below. In the previously described fundus oculi observation device 1, the light outputted from the observation light source 101 or the imaging light source 103 is projected to the eye E, and the fundus oculi reflection light is detected by the imaging element 10a or the imaging element 12a.

The arithmetic and control device 200 obtains the intensity distribution of the fundus oculi reflection light on the eye E based on the detected result, and then determines the projection position of the signal light LS based on the intensity distribution. These processes can be executed as in the above embodiment.

Furthermore, the arithmetic and control device 200 controls the scanning unit 141 to project the signal light LS toward the determined projection position. The fundus oculi reflection light of this signal light LS is superimposed with the reference light LR having been passed through the reference mirror 174, whereby then interference light LC is generated. The spectrometer 180 detects the spectral components of the interference light LC. The arithmetic and control device 200 forms a tomographic image or 3-dimensional image of the fundus oculi Ef based on the detected results.

Another example will be described with an optical image measurement device having a function of acquiring an OCT image and also a function as a scanning laser ophthalmoscope (SLO). In this case, it is possible to configure to determine the projection position of the signal light by using a laser beam outputted from a light source (such as a semiconductor laser, a He—Ne laser and an Ar laser) on the SLO side. At this moment, the laser light is projected to various positions in an eye by using a scanning mechanism on the SLO side, and the reflected lights at the respective positions are detected, whereby the intensity distribution of the reflected lights of the laser beam in the eye is obtained. The remaining processes are the same as aforementioned.

Thus, in the case of configuring to determine the projection position of a signal light by using a light other than an interference light based on a low-coherence light, it is possible, as in the above embodiment, to easily acquire a clear OCT image even when an eye has a site reducing the intensity of the signal light. The projection position of the signal light can be determined by using any light other than those in the above examples.

In the embodiment described above, an optical path length difference between an optical path of the signal light LS and an optical path of the reference light LR is changed by changing the position of the reference mirror 174, but the method for changing the optical path length difference is not limited to this. For instance, it is possible to change the optical path length difference by integrally moving the retinal camera unit 1A and the OCT unit 150 with respect to the eye E and changing the optical path length of the signal light LS. Further, it is also possible to change the optical path length difference by moving a measurement object in the depth direction (z-direction).

Although the fundus oculi observation device described in the above embodiment comprises an optical image measurement device of a Fourier-domain type, it is possible to apply, to the present invention, an optical image measurement device of any type such as a Time Domain type, a Full Field type and a Swept Source type.

Further, in the above embodiment, a device for acquiring OCT images of a fundus oculi is described. However, it is also possible to apply the configuration of the above embodiment to, for example, a device capable of acquiring OCT image of other locations of an eye such as the cornea.

[Program]

A program for controlling the device according to the present invention will be described. The control program 204a in the above embodiment is an example of this program.

This program is a program for controlling an optical image measurement device comprising the light generator and detector described above and also comprising a computer. The program is for making this computer function in the following manner: (1) a calculator for obtaining the intensity distribution of an interference light based on the result of detection by the detector; (2) a determining part for determining the projection position of a signal light to an eye based on this intensity distribution of the interference light; (3) an image forming part for forming an image of the eye based on the detection result of a new interference light based on a new signal light projected toward the projection position of the signal light and a new reference light having passed through a reference object.

With such a program, even if an eye has a site reducing the intensity of a signal light, it is possible to easily acquire a clear OCT image because the projection position of the signal light can be determined so as to avoid the site based on the intensity distribution of the interference light.

[Optical Image Measurement Method]

An optical image measurement method according to the present invention will be described. This optical image measurement method comprises the steps of: (1) generating an interference light by splitting a low-coherence light into a signal light and a reference light and superimposing the signal light having passed through an eye and the reference light having passed through a reference object; (2) detecting the generated interference light; (3) obtaining the intensity distribution of the interference light in the eye based on the detection result; (4) determining the projection position of the signal light to the eye based on the obtained intensity distribution; (5) projecting a new signal light based on a new low-coherence light toward the determined position; (6) generating a new interference light by superimposing the new signal light having passed through the eye and a new reference light based on the new low-coherence light; (7) detecting the generated new interference light; and (8) forming an image of the eye based on the detection result of the new interference light.

This optical image measurement method is implemented by, for example, the fundus oculi observation device 1 according to the above embodiment (optical image measurement device). According to such an optical image measurement method, even if an eye has a site reducing the intensity of a signal light, it is possible to easily acquire a clear OCT image because the projection position of the signal light can be determined so as to avoid the site based on the intensity distribution of the interference light.

Another optical image measurement method according to the present invention will be described. This optical image measurement method comprises the steps of: (1) projecting a light to an eye and detecting the light reflected by the eye; (2) obtaining the intensity distribution of the reflected light in the eye based on the detection result; (3) determining the projection position of a signal light to the eye based on the obtained intensity distribution; (4) generating an interference light by splitting a low-coherence light into a signal light and a reference light, projecting the signal light to the determined projection position, and superimposing the signal light having passed through the eye and the reference light having passed through a reference object; (5) detecting the generated interference light; and (6) forming an image of the eye based on the detection result of the interference light.

This optical image measurement method is implemented by, for example, the optical image measurement device described in the modification of the above embodiment. According to such an optical image measurement method, even if an eye has a site reducing the intensity of a signal light, it is possible to easily acquire a clear OCT image because the projection position of the signal light can be determined so as to avoid the site based on the intensity distribution of the interference light.

What is claimed is:

1. An optical image measurement device comprising:
   an interference-light generator configured to generate an interference light by splitting a low-coherence light into a signal light and a reference light and superimposing the signal light having passed through an eye and the reference light having passed through a reference object;
   a detector configured to detect the generated interference light;

a calculator configured to obtain intensity distribution of the interference light in the eye, based on a result of the detection by the detector;

a determining part configured to specify a region of smaller intensity than a threshold in the obtained intensity distribution and to determine a projection position of the signal light to the eye to exclude a specified area from the projection position; and an image forming part configured to form an image of the eye, based on a result of detection of a new interference light based on a new signal light projected toward the determined projection position and a new reference light having passed through the reference object.

2. The optical image measurement device according to claim 1, further comprising:

a changing part configured to change relative positions of the eye and the device so that the new signal light is projected to the projection position determined by the determining part.

3. The optical image measurement device according to claim 2, wherein:

the changing part includes a presenting part configured to present a fixation target for fixing the eye so that the new signal light is projected to the projection position determined by the determining part.

4. The optical image measurement device according to claim 3, wherein:

the presenting part includes a fixation-target display configured to display the fixation target, and a projection optical system configured to project the displayed fixation target onto a fundus oculi of the eye.

5. The optical image measurement device according to claim 2, wherein:

the determining part specifies a region with an intensity lower than a specific threshold value in the intensity distribution of the interference light obtained by the calculator, and determines at least part of a region other than the specified region as the projection position.

6. The optical image measurement device according to claim 2, wherein:

the determining part specifies a region with an intensity larger than a specific threshold value in the intensity distribution of the interference light obtained by the calculator, and determines at least part of the specified region as the projection position.

7. The optical image measurement device according to claim 2, wherein:

the changing part changes the relative positions so that the signal light is projected to the projection position determined by the determining part with respect to an image formed in the past.

8. The optical image measurement device according to claim 7, further comprising:

a display configured to display an image formed by the image forming part; and an operating part, wherein:

when the displayed image is designated by the operating part, the changing part changes the relative positions so that the signal light is projected to the projection position determined in formation of the designated image.

9. The optical image measurement device according to claim 7, wherein: the changing part includes a storage configured to store information on the projection position determined by the determining part, and changes the relative positions based on the stored information.

10. The optical image measurement device according to claim 1, wherein:

the determining part specifies a region with an intensity lower than a specific threshold value in the intensity distribution of the interference light obtained by the calculator, and determines at least part of a region other than the specified region as the projection position.

11. The optical image measurement device according to claim 1, wherein:

the determining part specifies a region with an intensity larger than a specific threshold value in the intensity distribution of the interference light obtained by the calculator, and determines at least part of the specified region as the projection position.

12. The optical image measurement device according to claim 1, further comprising:

a reporting part configured to, after a distance between the projection position determined by the determining part and a specific reference position is obtained, output reporting information based on the distance.

13. The optical image measurement device according to claim 12, wherein: the reporting part includes a display configured to display the image formed by the image forming part and the obtained distance as the reporting information.

14. The optical image measurement device according to claim 12, wherein: when the obtained distance is equal to or more than a specific distance, the reporting part outputs information showing that the obtained distance is equal to or more than the specific distance, as the reporting information.

15. An optical image measurement device comprising:

an optical system configured to project a light to an eye and detect a light reflected by the eye;

a calculator configured to obtain intensity distribution of the reflected light in the eye, based on a result of the detection by the optical system;

a determining part configured to specify a region of smaller intensity than a threshold in the obtained intensity distribution and to determine a projection position of a signal light to the eye to exclude a specified area from the projection position;

an interference-light generator configured to generate an interference light by splitting a low-coherence light into a signal light and a reference light, projecting the signal light to the determined projection position, and superimposing the signal light having passed through the eye and the reference light having passed through a reference object;

a detector configured to detect the generated interference light; and an image forming part configured to form an image of the eye, based on a result of the detection of the interference light.

16. An optical image measurement method comprising:

generating an interference light by splitting a low-coherence light into a signal light and a reference light and superimposing the signal light having passed through an eye and the reference light having passed through a reference object;

detecting the generated interference light;

obtaining intensity distribution of the interference light in the eye based on a result of the detection;

determining a projection position of the signal light to the eye to exclude a specified area from the projection position;

projecting a new signal light based on a new low-coherence light toward the determined projection position;

generating a new interference light by superimposing a new signal light having passed through the eye and a new reference light based on the new low-coherence light;

detecting the generated new interference light; and forming an image of the eye, based on a result of the detection of the new interference light.

17. An optical image measurement method comprising:

projecting a light to an eye and detecting a light reflected by the eye;

obtaining intensity distribution of the reflected light in the eye based on a result of the detection;

determining a projection position of the signal light to the eye to exclude a specified area from the projection position;

generating an interference light by splitting a low-coherence light into a signal light and a reference light, projecting the signal light to the determined projection position, and superimposing the signal light having passed through the eye and the reference light having passed through a reference object;

detecting the generated interference light; and forming an image of the eye based on a result of the detection of the interference light.

* * * * *